US00PP18651P2

(12) United States Plant Patent

Nicholls

(10) Patent No.: US PP18,651 P2

(45) Date of Patent: Mar. 25, 2008

(54) *PHILADELPHUS* PLANT NAMED 'STARBRIGHT'

(50) Latin Name: *Philadelphus×hybrida*
Varietal Denomination: STARBRIGHT

(76) Inventor: Wilf Nicholls, Memorial University of Newfoundland, St. John's, Newfoundland (CA), A1C 5S7

( * ) Notice: Subject to any disclaimer, the term of this patent is extended or adjusted under 35 U.S.C. 154(b) by 20 days.

(21) Appl. No.: 11/633,732

(22) Filed: Dec. 6, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—S. B. McCormick-Ewoldt

(57) ABSTRACT

A new cultivar of *Philadelphus* plant named 'STARBRIGHT' that is characterized by bronzy-purple emerging foliage, compact size, dark purplish-black calyx and pure white flowers. In combination these traits set 'STARBRIGHT' apart from all other existing varieties of *Philadelphus* known to the inventor.

4 Drawing Sheets

Genus: *Philadelphus.* Species: ×*hybrida.*
Denomination: 'STARBRIGHT'.

BACKGROUND OF THE INVENTION

The present invention relates to a new and distinct cultivar of mock orange that is grown as a shrub in the landscape. The new cultivar is known botanically as *Philadelphus*× *hybrida* and will be referred to hereinafter by the cultivar name 'STARBRIGHT'.

'STARBRIGHT' was selected by the inventor in Vancouver, British Columbia, Canada, in 1995 for unique foliage and calyx color. The new cultivar 'STARBRIGHT' is a hybrid plant that resulted from cross-pollination breeding project begun in 1990 and conducted by the inventor in a cultivated area of Vancouver, British Columbia, Canada. Reciprocal crosses were made using emasculated flowers of an individual plant of seed parent *Philadelphus delavayi* ssp *melanocalyx* (unpatented) and an individual plant of pollen parent *Philadelphus lewisii* (unpatented).

'STARBRIGHT' is a deciduous shrub characterized by the bronzy-purple newly emerging foliage and a purplish-black calyx. It is smaller in height and more hardy than its parent *Philadelphus delavayi* and has larger flowers than its parent *Philadelphus lewisii.* This combination of the characteristics of foliage color, size, hardiness and flower size distinguish 'STARBRIGHT' from all other *Philadelphus* known to the inventor.

'STARBRIGHT' resembles its seed parent *Philadelphus delavayi* ssp. *melanocalyx* but differs in that the parent has a hardiness rating of USDA Zone 6 while the resulting hybrid is hardy to USDA Zone 3, greatly expanding the range of this plant. Flower size of 'STARBRIGHT' is larger than the flower size of either parent. Plant height of 'STARBRIGHT' is lower than *Philadelphus delavayi.* Petals of 'STARBRIGHT' overlap while those of the *lewsii* parent have a gap between the petals. No seedlings have ever arisen from this hybrid which appears to be sterile.

The first asexual reproduction of 'STARBRIGHT' was conducted by the inventor in 1996 in a cultivated area of Vancouver, British Columbia, Canada. The method used for asexual propagation was semi-hardwood cuttings. Since that time the inventor has determined that distinguishing characteristics of 'STARBRIGHT' are stable and are reproduced true to type in successive generations of asexual reproduction.

SUMMARY OF THE INVENTION

The following traits have been repeatedly observed and represent the characteristics of the new *Philadelphus* cultivar 'STARBRIGHT'. These traits in combination distinguish 'STARBRIGHT' from all other commercial varieties of *Philadelphus* known to the inventor. 'STARBRIGHT' has not been tested under all possible conditions and phenotypic differences may be observed with variations in environmental, climatic and cultural conditions, without however, any variance in genotype.

1. *Philadelphus* 'STARBRIGHT' is a deciduous shrub.
2. *Philadelphus* 'STARBRIGHT' is suitable for use in the landscape.
3. *Philadelphus* 'STARBRIGHT' has large white flowers in the spring.
4. *Philadelphus* 'STARBRIGHT' exhibits a dense, upright habit.
5. *Philadelphus* 'STARBRIGHT' exhibits foliage that is bronzy-purple when newly emerged.
6. *Philadelphus* 'STARBRIGHT' has a purplish-black calyx.
7. *Philadelphus* 'STARBRIGHT' is propagated using vegetative cuttings.
8. *Philadelphus* 'STARBRIGHT' is hardy to USDA Zone 3a.
9. *Philadelphus* 'STARBRIGHT' achieves 3 m in height and 2 m in width.

BRIEF DESCRIPTION OF THE DRAWINGS

The accompanying colored photographs illustrate the overall appearance of the new variety.

Figure 1:
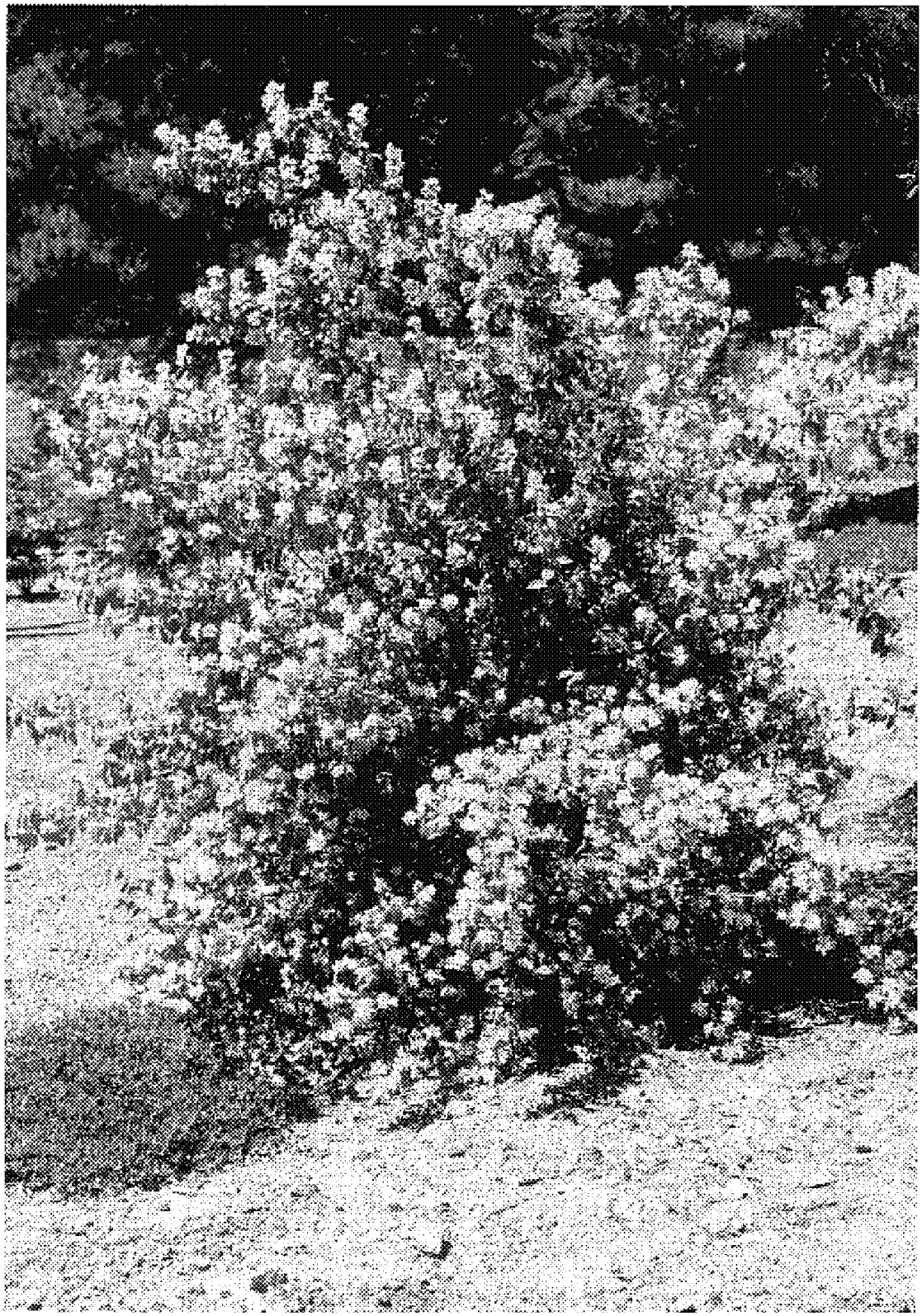
FIG. 1 shows a whole plant of 'STARBRIGHT' growing in the ground in Vancouver, British Columbia, Canada. The plant shown is five years old.
Figure 2:
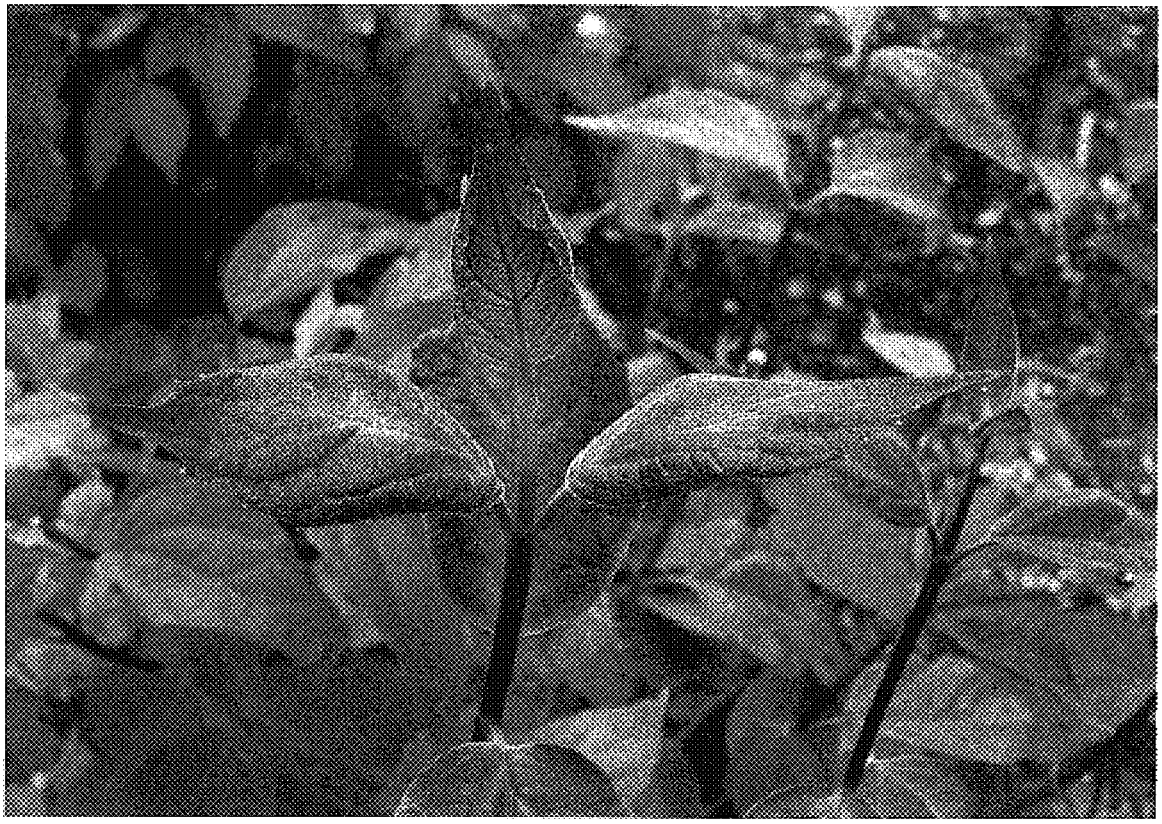
FIG. 2 shows a close-up view of the current year's near foliage growth on the plant depicted in FIG. 1.
Figure 3:
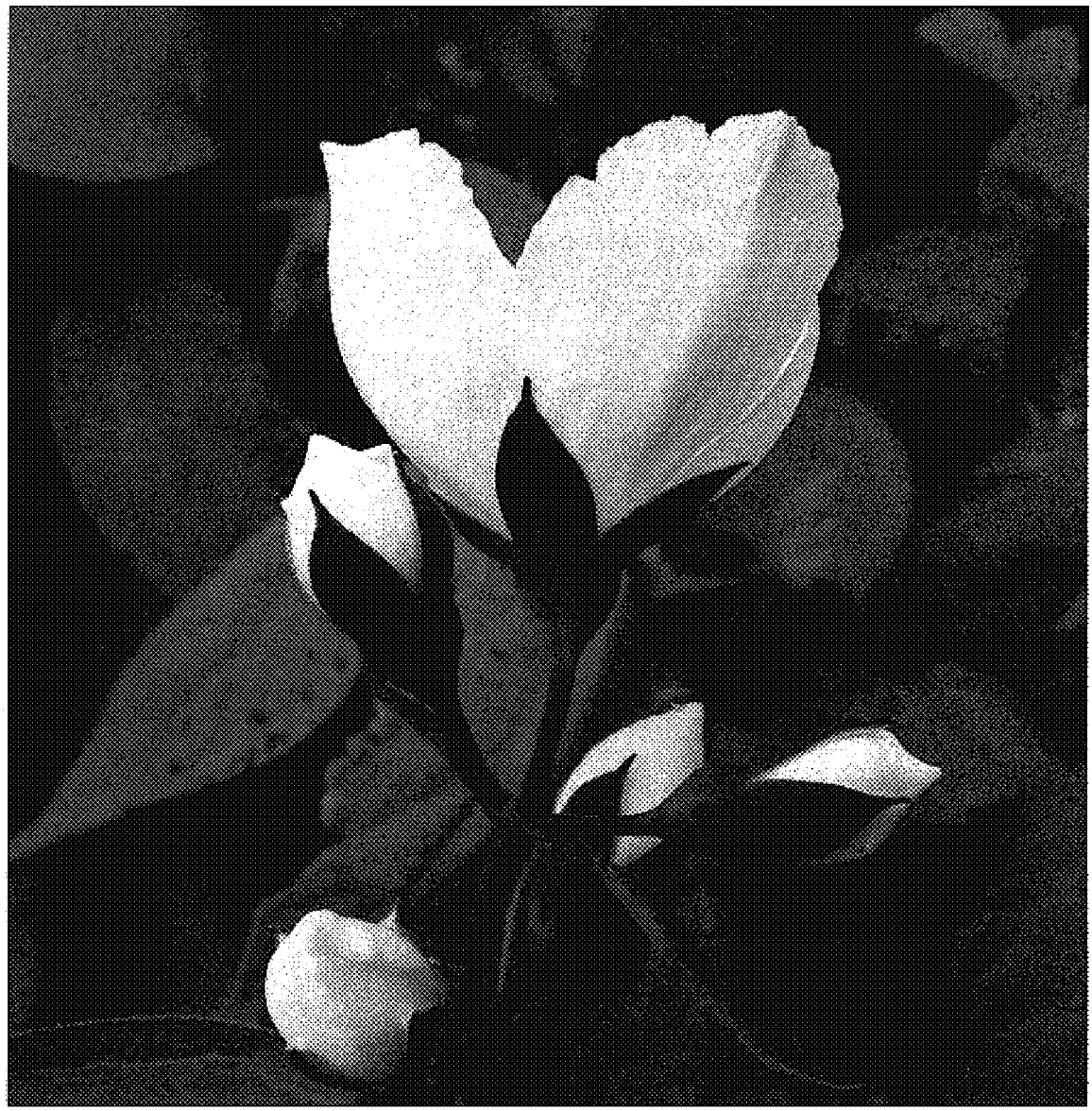
FIG. 3 shows a side view of several flowers showing the dark calyx.
Figure 4:
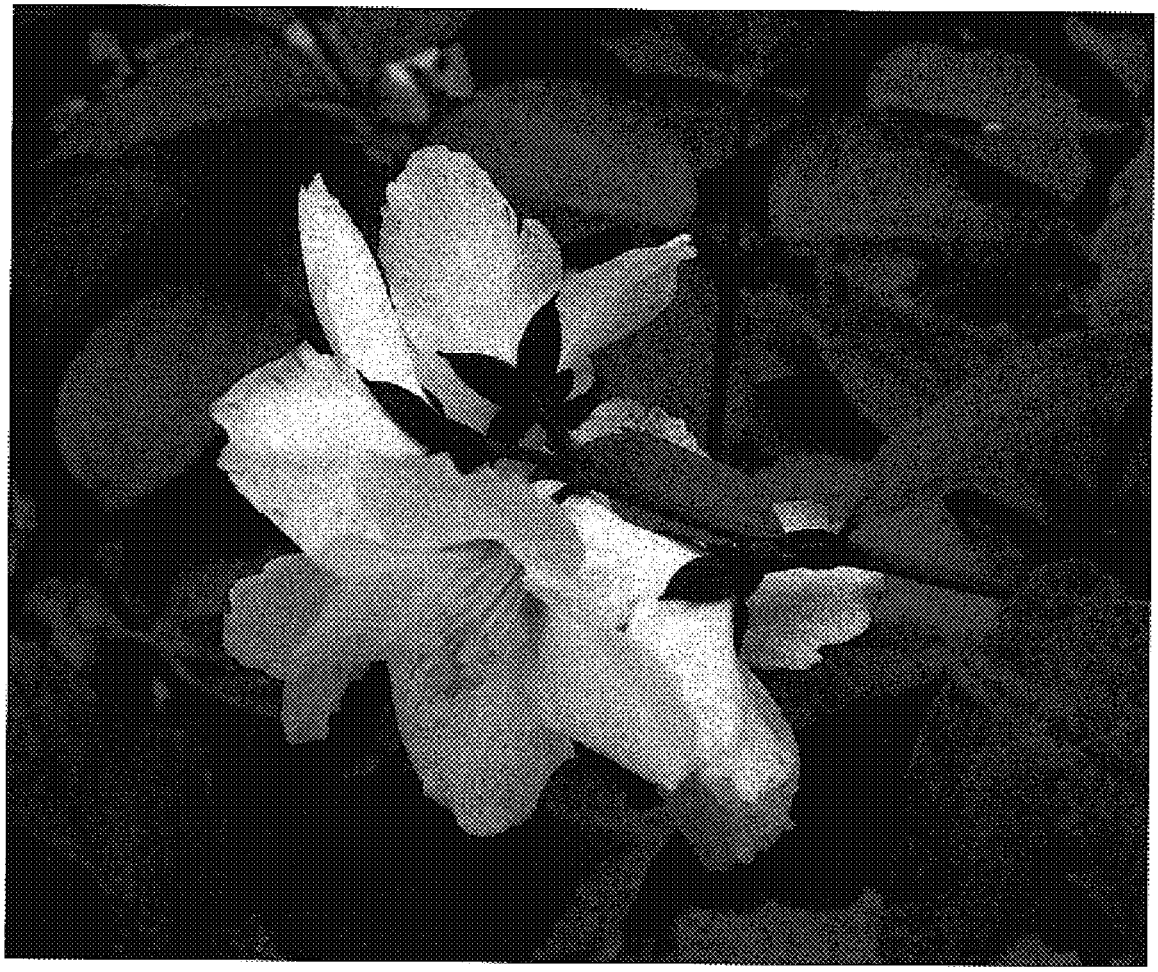
FIG. 4 shows petals and reproductive organs of a flower.

The prints are made using conventional photographic techniques and although foliage colors in photographs may appear different from actual colors due to light reflectance, they are as accurate as possible by conventional photography.

BOTANICAL DESCRIPTION OF THE PLANT

The following is a detailed description of a 6 year old specimen of 'STARBRIGHT' as grown in the ground, out-of-doors in St. John's, Newfoundland, Canada. The color determinations are in accordance with the 2001 Edition of the Colour Chart of The Royal Horticultural except where general color terms of ordinary dictionary significance are used. The growing requirements are similar to the species.

Botanical classification:
- *Genus.*—*Philadelphus.*
- *Species.*—×*hybrida.*
- *Denomination.*—'STARBRIGHT'.

Commercial classification: Deciduous shrub.
Use: Plant for use in landscape.
Common name: Mock orange.
Commercial container size: 3 gallon container.
Cultural requirements: Plant in full sun in well-drained soil with moderate to regular water.
Parentage: *Philadelphus* 'STARBRIGHT' is a hybrid plant that resulted from cross-pollination of the following parents:
- *Pollen parent.*—*Philadelphus lewisii.*
- *Seed parent.*—*Philadelphus delavayi* ssp. *melanocalyx.*

Plant description:
- *Bloom period.*—Late spring to early summer.
- *Plant habit.*—Upright habit.
- *Vigor.*—Moderate.
- *Root system.*—Fibrous roots.
- *Plant dimensions* (*first year*).—80 cm to 100 cm in height and 30 cm in width.
- *Plant dimensions* (*3 years*).—1.5 m in height and 1 m in width.
- *Plant dimensions* (*maturity*).—3 m in height, 2 m in width.
- *Growth rate.*—New basal stems may exceed 2 m in one season on mature plants.
- *Hardiness.*—USDA Zone 3a.
- *Propagation.*—Softwood to semi-hardwood cuttings or tissue culture.
- *Rooting time.*—6 to 8 weeks is needed for an initial cutting to develop roots.
- *Crop time.*—3 years are needed to produce a commercial 3 gallon container from a rooted cutting.
- *Pest and disease resistance and susceptibility.*—None noted.

Stems:
- *Branching habit.*—Multiple stems and branching; branches opposite.
- *Color.*—152B to N199C.
- *Shape.*—Terete.
- *Diameter.*—6 mm (main stem), 2 mm (secondary stems).
- *Length* (*main stems*).—Up to 2 m for new basal stems.
- *Length* (*secondary stems*).—Up to 1 m.
- *Internode length.*—6 cm to 10 cm on main stems; 2.5 cm to 5.5 cm on secondary and flowering stems.
- *Surface.*—Glabrous.

Foliage:
- *Leaf arrangement.*—Opposite.
- *Leaf division.*—Simple.
- *Leaf shape.*—Lanceolate to elliptical.
- *Leaf dimensions.*—7 cm to 12.5 cm in length and 3.5 cm to 7 cm in width.
- *Leaf tip.*—Apiculate to caudate.
- *Leaf base.*—Rounded to attenuate.
- *Quantity of leaves per stem.*—3 to 4 pairs on flowering branches; numerous on first-year basal growths.
- *Leaf venation pattern.*—Pinnate.
- *Vein color* (*adaxial*).—152B to 136A.
- *Vein color* (*abaxial*).—152B.
- *Margin type.*—Shallowly and widely serrated.
- *Leaf surface* (*adaxial*).—Slightly pubescent; dense silvery to whitish pubescence when young but later just a few stiff hairs.
- *Leaf surface* (*abaxial*).—Slightly pubescent; dense silvery to whitish pubescence when young but later just a few stiff hairs; veins remain slightly pubescent.
- *Young leaf color* (*adaxial and abaxial*).—187A to N77A.
- *Mature leaf color* (*adaxial*).—137A to 136A.
- *Mature leaf color* (*abaxial*).—137C.
- *Leaf attachment.*—Petiolate.
- *Petiole dimensions.*—10 mm in length and 2 mm in diameter.
- *Petiole surface.*—Sparsely pubescent.
- *Pubescence features.*—White hairs less than 1 mm in length.
- *Petiole color.*—N77A to 200B.

Inflorescence:
- *Inflorescence form.*—Terminal raceme with lowest flowers axillary.
- *Flower arrangement.*—Flowers held at 40 to 50 degrees from main axis.
- *Quantity of flowers per inflorescence.*—3 to 7.
- *Quantity of flowers per plant.*—Numerous on 3 year old stems.

Flowers:
- *Flower aspect.*—Flowers face outwards to upwards.
- *Diameter of flower.*—5.2 cm to 5.6 cm.
- *Depth of flower.*—1 cm.
- *Bud shape.*—Rounded, pyramidal.
- *Bud color.*—77A to 200A.
- *Bud surface.*—Sparsely pubescent to glabrescent.
- *Bud pubescence.*—Hairs white, 1 mm in length.
- *Bud dimensions.*—13 mm in length and 5 mm in diameter.
- *Corolla dimensions.*—24 mm to 27 mm in length and 20 mm to 23 mm in width.
- *Corolla tube.*—Not present.
- *Petal margins.*—Entire, slightly undulating.
- *Petals fused or unfused.*—Unfused.
- *Petal shape.*—Oval to obovate; rounded to obtuse apex.
- *Number of petals.*—Four.
- *Petal color* (*adaxial and abaxial*).—155D.

*Petal surface* (*adaxial and abaxial*).—Glabrous.
*Peduncle dimensions.*—10 mm in length and 1 mm in width.
*Peduncle shape.*—Terete.
*Peduncle color.*—N77A to 152B.
*Peduncle surface.*—Slightly pubescent to glabrescent.
*Peduncle pubescence.*—Hairs white, less than 1 mm in length.
*Calyx shape.*—Deltoid.
*Calyx dimensions.*—8 mm to 10 mm in length and 5 mm in diameter.
*Number of sepals.*—Four.
*Sepals fused or unfused.*—Unfused.
*Sepal color* (*adaxial*).—139C to 146C.
*Sepal color* (*abaxial*).—77A to 200A.
*Sepal surface* (*adaxial*).—Densely pubescent with short white hairs.
*Sepal surface* (*abaxial*).—Glabrous.

Reproductive organs:
*Pistil.*—3 to 4, fused towards the base.
*Pistil shape.*—Terete.
*Pistil dimensions.*—8 mm to 10 mm in length.
*Pistil color.*—155D.
*Pistil surface.*—Glabrous.
*Stigma shape.*—Oblong; flattened.
*Stigma dimensions.*—3 mm in length and 1 mm in width.
*Stigma color.*—155D.
*Style shape.*—Terete.
*Style dimensions.*—6 mm to 7 mm in length and 1 mm in width.
*Style color.*—155D.
*Number of stamens.*—25 to 30.
*Stamens* (*fused or unfused*).—Unfused; tetradynamous.
*Stamen dimensions.*—4 mm to 13 mm in length and 1 mm in width.
*Stamen color.*—155D.
*Anther shape.*—Linear; basifixed.
*Anther dimensions.*—2 mm in length and 1 mm in width.
*Anther color.*—12A.
*Pollen color.*—12A.
*Pollen amount.*—Copious.
*Ovary position.*—Epigynous.
*Ovary color.*—77A to 200A.

Seed: No seed has been observed; plant appears to be sterile.

It is claimed:

1. A new and distinct cultivar of *Philadelphus* plant named 'STARBRIGHT', as described and illustrated here within.

* * * * *